(12) United States Patent
Mohl

(10) Patent No.: US 10,426,619 B2
(45) Date of Patent: Oct. 1, 2019

(54) IMPLANT AND METHOD FOR IMPROVING COAPTATION OF AN ATRIOVENTRICULAR VALVE

(71) Applicant: Werner Mohl, Altenmarkt/Thennenberg (AT)

(72) Inventor: Werner Mohl, Altenmarkrt/Thennenberg (AT)

(73) Assignee: AVVIE GMBH, Vienna (AT)

( * ) Notice: Subject to any disclaimer, the term of this patent is extended or adjusted under 35 U.S.C. 154(b) by 567 days.

(21) Appl. No.: 14/984,456

(22) Filed: Dec. 30, 2015

(65) Prior Publication Data

US 2017/0189186 A1    Jul. 6, 2017

(51) Int. Cl.
*A61F 2/24* (2006.01)

(52) U.S. Cl.
CPC .......... *A61F 2/2454* (2013.01); *A61F 2/2445* (2013.01); *A61F 2/2466* (2013.01); *A61F 2/2457* (2013.01); *A61F 2210/0014* (2013.01); *A61F 2230/0006* (2013.01); *A61F 2230/0013* (2013.01); *A61F 2310/00023* (2013.01)

(58) Field of Classification Search
CPC ...... A61F 2/243; A61F 2/2442; A61F 2/2445; A61F 2/2451; A61F 2/2454; A61F 2/2457; A61F 2/2463; A61F 2/2466
USPC ........................................................ 623/2.11
See application file for complete search history.

(56) References Cited

U.S. PATENT DOCUMENTS

| | | |
|---|---|---|
| 2005/0070999 A1 | 3/2005 | Spence |
| 2015/0039083 A1 | 2/2015 | Rafiee |
| 2015/0230919 A1 | 8/2015 | Chao et al. |

FOREIGN PATENT DOCUMENTS

WO    2015/052570 A1    4/2015

*Primary Examiner* — Melanie R Tyson
(74) *Attorney, Agent, or Firm* — Fitch, Even, Tabin & Flannery LLP

(57) ABSTRACT

An implant for improving coaptation of an atrioventricular valve in which the atrioventricular valve has a first native leaflet, a second native leaflet and an annulus includes a support structure configured to be arranged on and fixed to the annulus or to at least one of the first and second native first leaflets. The implant also includes flexible retention structure mounted to the support structure so as to prevent prolapse of the at least one of the first and second native leaflets. A method for improving coaptation of such an atrioventricular valve is also disclosed.

7 Claims, 9 Drawing Sheets

IMPLANT AND METHOD FOR IMPROVING COAPTATION OF AN ATRIOVENTRICULAR VALVE

FIELD

The invention relates to an implant and a method for improving coaptation of an atrioventricular valve.

BACKGROUND

Atrioventricular valves are membranous folds that prevent backflow from the ventricles of the human heart into the atrium during systole. They are anchored within the ventricular cavity by chordae tendineae, which prevent the valve from prolapsing into the atrium.

The chordae tendineae are attached to papillary muscles that cause tension to better hold the valve. Together, the papillary muscles and the chordae tendineae are known as the subvalvular apparatus. The function of the subvalvular apparatus is to keep the valves from prolapsing into the atria when they close. The opening and closure of the valves is caused by the pressure gradient across the valve.

The human heart comprises two atrioventricular valves, the mitral valve and the tricuspid valve. The mitral valve allows the blood to flow from the left atrium into the left ventricle. The tricuspid valve is located between the right atrium and the right ventricle. The mitral valve has two leaflets that are each divided into several scallops: the anterior leaflet has three scallops (A1, A2, A3), the posterior leaflet has three scallops (P1, P2, P3). The tricuspid valve has three leaflets. Engagement of corresponding surfaces of the leaflets against each other is decisive for providing closure of the valve to prevent blood flowing in the wrong direction. The closure forms a so called coaptation area.

Native heart valves become dysfunctional for a variety of pathological causes. Failure of the leaflets to seal during ventricular systole is known as malcoaptation, and may allow blood to flow backward through the valve (regurgitation). Malcoaptation is often caused by a dilatation of the annulus. This is mainly due to an enlargement of the left atrium with preserved posterior wall motion or in case of posterior myocardial infarction due to posterior wall motion abnormalities leading to asymmetric annular dilatation. Another reason is a restriction in motion or an excessive motion of the leaflet structures. Another cause of severe regurgitation is the local elongation or rupture of chordae resulting in a prolapse of parts of the leaflet. Heart valve regurgitation can result in cardiac failure, decreased blood flow, lower blood pressure, and/or a diminished flow of oxygen to the tissues of the body. Mitral regurgitation can also cause blood to flow back from the left atrium to the pulmonary veins, causing congestion and backward failure.

Some pathologies of atrioventricular valves, such as malcoaptation, often require reconstruction of the valvular and subvalvular apparatus as well as redesigning the enlarged annulus. Sometimes a complete surgical replacement of the natural heart valve with heart valve prosthesis is necessary. There are two main types of artificial heart valves: the mechanical and the biological valves. The mechanical-type heart valve uses a pivoting mechanical closure supported by a base structure to provide unidirectional blood flow. The tissue-type valves have flexible leaflets supported by a base structure and projecting into the flow stream that function similar to those of a natural human heart valve and imitate their natural flexing action to coapt against each other. Usually two or more flexible leaflets are mounted within a peripheral support structure made of a metallic or polymeric material. In transcatheter implantation the support within the annulus may be in the form of a stent, as is disclosed in US 2011/0208298 A1.

In order to provide enough space for the artificial leaflets to work properly, the peripheral support is positioned in the native valve so as to force the native leaflets apart. To this end and in order to provide appropriate anchoring of the peripheral support within the native valve, the same is fixed to the native leaflets by suitable means. However, in some applications, such as with mitral valves, fixing the peripheral support to the native anterior leaflet and dislocating the same from its natural position may cause an obstruction of the outflow tract and of the aortic valve, which is located in the left ventricle immediately adjacent the anterior leaflet.

The gold standard for treating mitral regurgitation is to repair the mitral apparatus including leaflets and the subvalvular apparatus and to reshape the mitral annulus (Carpentier technique). If repair is not possible an excision of the valve including parts of the subvalvular apparatus is performed with subsequent implantation of a heart valve prosthesis. This is necessary particularly when the valve is destructed by inflammation. Although in most instances a complete excision of the destroyed valve is necessary, sometimes a partial replacement is possible. A clinically used mitral valve restoration system (Mitrofix®) replaces only the posterior leaflet with a rigid prosthesis mimicking a fixed posterior leaflet allowing the natural anterior leaflet to coapt. This prosthesis is also sewn into the position of the destroyed posterior aspect of the annulus. This requires open heart surgery and extended cardiac arrest.

Recent trends focus on less invasive procedures to minimize surgical trauma and to perform transcatheter approaches including transatrial, transaortal or transapical procedures to replace or reconstruct dysfunctional valves thus minimizing the need of or avoiding heart lung machine and cardiac arrest. Whereas this is a common procedure in aortic valves nowadays, only few mitral valves insufficiencies are corrected by percutaneous or transapical procedures. Most of these concepts are redesigning and remodeling artificially the mitral annulus to allow coaptation or to enforce coaptation by fixing both leaflets together with a clip reducing mitral regurgitant flow. Percutaneously or transapically deployed valve prostheses are difficult to anchor due to the special anatomy of the mitral valve and the vicinity of the anterior leaflet to the aortic outflow tract.

SUMMARY

Therefore, it is an object of the instant invention to provide an improved implant for improving coaptation of an atrioventricular valve and to prevent prolapse of the native leaflet into the atrium. In particular, it is an object of the invention to provide an implant that does not involve the risk of stenosis of the aortic valve.

It is a further object of the invention to provide an implant that can be easily deployed to the target site.

The invention generally provides improved medical implants and methods for the treatment of regurgitation in atrioventricular valves, in particular mitral valves. In some embodiments, the invention provides a medical implant that provides retention means cooperating with at least one of the first and second native leaflet in order to prevent a prolapse thereof into the atrium. Therefore, the implant assists the function of a damaged or otherwise malfunctional native leaflet. However, the damaged or otherwise malfunctional native leaflet is not physically removed. Rather, the damaged or otherwise malfunctional native leaflet is left in the valve.

The implant provides retention means that prevent the damaged or otherwise malfunctional native leaflet from prolapsing into the atrium. The retention means may or may not comprise an artificial leaflet that is arranged adjacent the native leaflet. The retention means may comprise a flexible net or flexible wires or yarns that cooperate with the artificial leaflet or the native leaflet in order to prevent prolapse. In case an artificial leaflet is provided, the damaged or otherwise malfunctional native leaflet may support the function of the artificial leaflet or parts thereof.

In some embodiments, the retention means are flexible in order to allow the native and/or artificial leaflet to perform its usual function and coapt with the other native leaflet.

In some embodiments, the invention provides an implant comprising a support structure configured to be arranged on and fixed to the annulus or to at least one of the first and second native first leaflets, the implant further comprising retention means fixed to the support structure so as to prevent prolapse of the at least one native leaflet or parts thereof (e.g. P1, P2, P3), wherein the support structure comprises an upper support element to be arranged on a superior surface of the annulus or of the at least one native leaflet and a lower support element to be arranged on an inferior surface of the annulus or of the at least one native leaflet, the upper and the lower support elements each comprising connection means cooperating which each other for interconnecting the upper and the lower support element while clamping a section of the annulus or of the at least one native leaflet between the upper support element and the lower support element, wherein at least one connection means comprises a penetrating section configured to penetrate the annulus or the at least one native leaflet for being connected with the other connection means.

Thus, the support structure is fixed on the annulus of the native valve or on at least one of the first and second native leaflet. Preferably, the support structure is fixed only to the first native leaflet or the second native leaflet. In case of an implant configured for mitral valves, the first native leaflet is a posterior leaflet of the mitral valve and the second native leaflet is an anterior leaflet of the mitral valve. In case the retention means comprise an artificial leaflet, the latter is preferably configured as an artificial posterior leaflet and replaces and/or supports the function of the native posterior leaflet. The artificial posterior leaflet is preferably shaped such as to improve coaptation with the native anterior leaflet and may be adjusted individually based on patient-specific image data obtained by imaging techniques.

In case of an implant configured for tricuspid valves, the first native leaflet is an anterior leaflet of the tricuspid valve and the second native leaflet is a posterior leaflet and the third leaflet is the septal leaflet of the tricuspid valve. In case the retention means comprise an artificial leaflet, the latter is configured to replace the function of the native anterior or posterior leaflet. The artificial anterior or posterior leaflet or the combination of both is preferably shaped such as to improve coaptation with the native anterior and posterior leaflet.

The support structure is preferably fixed only to one leaflet, either the first or the second leaflet, or only to that partial region of the annulus, from which the first or the second leaflet emerges. Further, the retention means are configured to cooperate with and prevent prolapse of only the leaflet, to which the support structure is fixed.

The support structure is configured to carry the retention means and to hold the retention means in a position, in which it can retain the at least one native leaflet to coapt with the native second leaflet.

In order to associate the implant to the annulus or the native leaflet, the support structure comprises an upper support element and a lower support element configured to squeeze a section of the annulus or the native leaflet between them in order to avoid improper paravalvular leakage and regurgitation.

The upper support element preferably is substantially C-shaped, U-shaped, semicircular or circular so as to conform to the shape of the annulus or a section of the annulus. In order to stabilize the upper support element, the upper support element preferably comprises bracing means for applying a radial bracing force across the annulus and the adjacent atrial wall. The bracing force acts so as to spread apart the annulus, so as to firmly hold the upper support element relative to the annulus.

In some embodiments of the invention, the upper support element extends only over a segment of the annulus.

The upper and the lower support elements preferably comprise a foldable structure, so that it may be advanced to the valve in a folded state. Preferably, the upper and the lower support elements comprise curved wires made of a shape memory alloy, such as nitinol. Preferably, the curved wires are in the shape of at least two wings extending outwardly from a central support.

In some embodiments, the implant further comprises a tubular housing, wherein the support structure and the retention means are deployable from a first position, in which the support structure and the retention means are arranged within the tubular housing, into a second position, in which the support structure is deployed. In this way, the implant can be easily deployed to the heart by minimal invasive surgery or endovascular approaches. In particular, the tubular housing is preferably advanced into the heart by means of a catheter or a deployment instrument transatrially, transseptally, transfemorally or transapically.

Preferably, the support structure and the retention means are configured to be deployed from a folded or rolled-up state into an extended state. In the folded or rolled-up state, the structures may easily be advanced to the heart transcatheterally or transapically.

Preferably, the tubular housing comprises two half-shells, a first half-shell housing the upper support element and a second half-shell housing the lower support element. Alternatively, the tubular housing may comprise more than two shells, each extending over a segment of the circular cross section of the tubular housing and together forming the tubular housing.

The configuration of the tubular housing with two or more shells allows for a selective deployment of a corresponding number of elements of the implant. A preferred way of deploying the elements of the implant is achieved by having the shells, in particular the first and second half-shells, arranged to swing open. The swinging open of the shells allows to open the tubular housing for enabling a deployment of the implant.

Preferably, the upper and the lower support elements of the implant are housed in the tubular housing in a separate, not interconnected manner. Thus, the upper and the lower support elements, each preferably arranged in an own shell of the tubular housing, can easily be deployed separately and be separately brought in the correct position that subsequently allows their connection with each other.

Preferably, the first and second half-shells are arranged at the distal end of a deployment instrument, such as a steerable instrument or a catheter. The instrument may have a catheter-like tube that may be advanced transapically, transaortically or transatrially into the heart and that carries the tubular housing on its distal end. The proximal end of the deployment instrument, which is held by the surgeon or interventionist, may preferably be provided with actuation means cooperating with the shells of the tubular housing and with the upper and the lower support structure in order to control the swinging open of the shells and of the displacement, the deployment and the extension of the support elements.

In some embodiments, the retention means comprise an artificial leaflet arranged on the upper support element. Alternatively, or in addition, the retention means comprise a flexible net or a plurality of flexible wires or yarns. The flexible net or the plurality of flexible wires or yarns cover an area that corresponds substantially to the area of the native leaflet and/or the artificial leaflet to be held by the retention means. In some embodiments, the flexible net, wires or yarns may be embedded into or fixed to the artificial leaflet. Preferably, the retention means, in particular the flexible net, wires or yarns, are fixed to the native leaflet by means of at least one fixation element at the hinge point between the coaptation and free part of the native valve.

The artificial leaflet may be made of a biocompatible material, such as polyethylene or polyurethane, polyfluorethylen (Goretex®) or from natural tissue such as heterologic pericardium.

In a preferred embodiment the artificial net or leaflet structure is fixed with a second fixation mechanism at the hinge point of the prolapsing leaflet at the coaptation line with the native (prolapsing) leaflet part.

In order to fix the retention means on the supporting structure, a preferred embodiment provides that the lower support element carries at least one holding arm for holding the retention means. The holding arm may be configured in the form of a hook. The free end of the arm preferably carries an eye for drawing a wire or a yarn of the retention means therethrough.

Preferably, the retention means, on one end thereof, are connected to the lower support structure and, on the other end thereof, are connected to the upper support structure. In its region between the both ends the retention means cooperate with the native leaflet in order prevent a prolapse.

Preferably, the holding arm or the hook is configured to be adjustable in length in order to allow for some flexibility in application.

According to a further aspect the invention refers to a method of improving coaptation of an atrioventricular valve, the atrioventricular valve having an annulus, a first native leaflet and a second native leaflet, the method comprising:
providing an implant comprising a support structure and retention means fixed to the support structure, wherein the support structure comprises an upper support element and a lower support element, the implant being arranged in a tubular housing with the upper and the lower support structure being in a folded state, said tubular housing comprising a first and a second half-shell, wherein the first half-shell houses the upper support element and the second half-shell houses the lower support element,
advancing the tubular housing into the heart,
swinging open the half-shells,
advancing the tubular housing with the implant so that the first or the second native leaflet is arranged between the first and the second half-shells,
unfolding the upper and the lower support structure,
fixing the upper and the lower support structure relative to the annulus or to the first or second native leaflet, said fixing step comprising interconnecting connection means of the upper and the lower support elements thereby clamping a section of the annulus or of said first or second native leaflet between the upper support element and the lower support element, wherein at least one connection means comprises a penetrating section that penetrates the annulus or said first or second native leaflet when being connected with the other connection means,
positioning the retention means so as to prevent prolapse of the first or second native leaflet,
withdrawing the tubular housing from the heart.

Preferably, the tubular housing is advanced into the heart transatrially, i.e. through the left atrium of the heart, transseptally, i.e. through the septum of the heart, transfemorally or transapically, i.e. through the apex of the heart or the aorta. The positioning is facilitated by a steerable guiding element to maneuver the tubular housing.

Preferably, the step of fixing the support structure comprises positioning the upper support element on a superior surface of the annulus or the native leaflet and positioning the lower support element on an inferior surface of the annulus or the native leaflet.

Preferably, said fixing step comprises, before interconnecting the connection means, axially aligning the connection means with each other by moving at least one of the connection means relative to the other connection means.

Preferably, said step of interconnecting the connection means comprises moving the connection means towards each other by a closing action of the half-shells.

Preferably, the step of connecting the connection means with each other comprises penetrating the annulus or said first or second native leaflet. The penetration may be achieved by mechanic forces of a penetrating section of at least one connection means or by heat or by electric current.

Preferably, said step of positioning the retention means comprises adjusting a length of said retention means between one end thereof, which is connected to the lower support structure, and another end thereof, which is connected to the upper support structure.

Preferably, the native first leaflet is a native posterior leaflet of a mitral valve and the second native leaflet is an anterior leaflet of the mitral valve.

In a preferred embodiment retention means may be used, the size of which is chosen to fit the individual patient by measurements of the prolapsing areas of the native valve. In particular, the size of the support structure and/or the size of the retention means may be calculated from the size of the prolapsing native leaflet part of the patient.

Further, the length of the two arms of the support structure may be chosen as a function of individual measurements of the prolapsing areas of the valve.

Further, the retention means may be fixed to the native prolapsing leaflet at the coaptation line of the latter.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Figure 1:
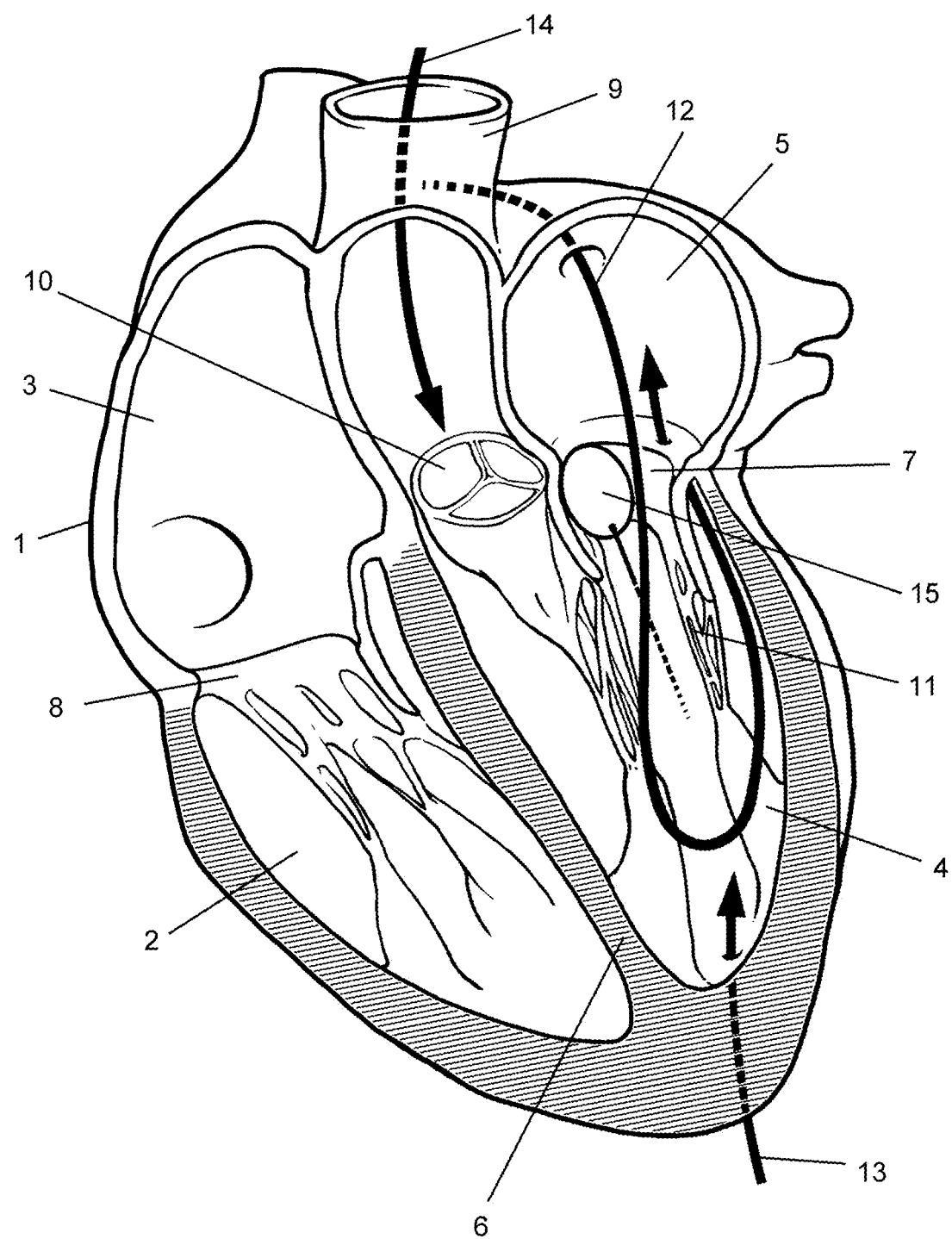
FIG. 1 is a schematic illustration of a human heart.

In FIG. 1 is a schematic illustration of a human heart 1 comprising the right ventricle 2, the right atrium 3, the left ventricle 4 and the left atrium 5. The septum 6 divides the heart 1 in a right and a left section. The mitral valve 7 allows the blood to flow from the left atrium 5 into the left ventricle 4. The tricuspid valve 8 is located between the right atrium 3 and the right ventricle 2. The ascending aorta 9 originates at the orifice of the aortic valve 10. The mitral valve 7 comprises an anterior leaflet and a posterior leaflet that are anchored within the left ventricular cavity by chordae tendineae 11, which prevent the valve 7 from prolapsing into the left atrium 5.

The mitral valve implant of the invention is configured to be deployed to the heart transcatheterally. In particular, the implant can be delivered to the heart by means of a catheter transatrially, i.e. through the left atrium of the heart, transseptally, i.e. through the septum 6 of the heart as depicted by line 12, transapically, i.e. through the apex of the heart as depicted by line 13, or through the ascending aorta 9 as depicted by line 14.

During the implant procedure a balloon 15 is placed into the orifice of the mitral valve 7, which is inflated during systole and deflated during diastole to minimize regurgitant volume flow and to prevent severe inflow into the pulmonary veins.

Figure 3:
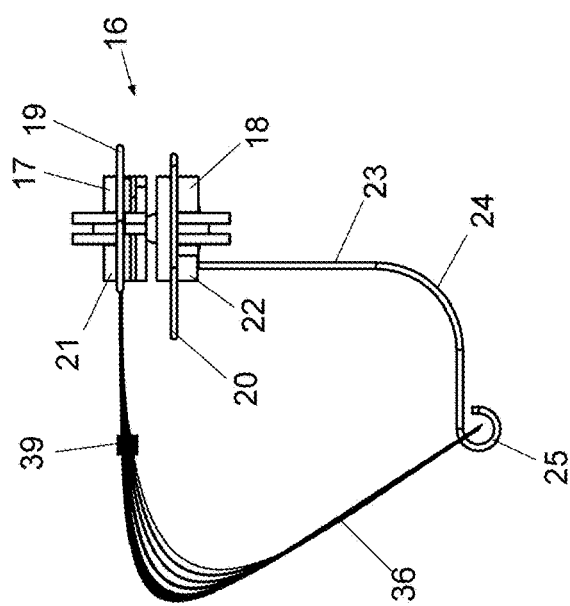
FIG. 3 is a side view of the mitral valve implant of FIG. 2.
Figure 4:
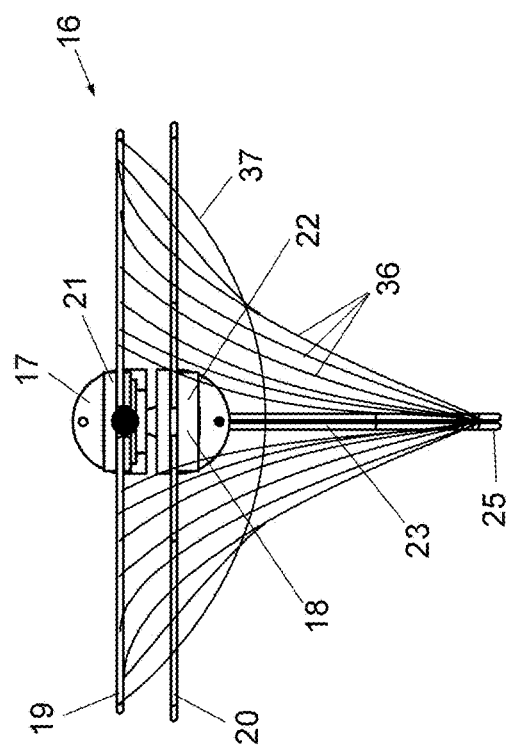
FIG. 4 is a front view of the mitral valve implant of FIG. 2.
Figure 2:
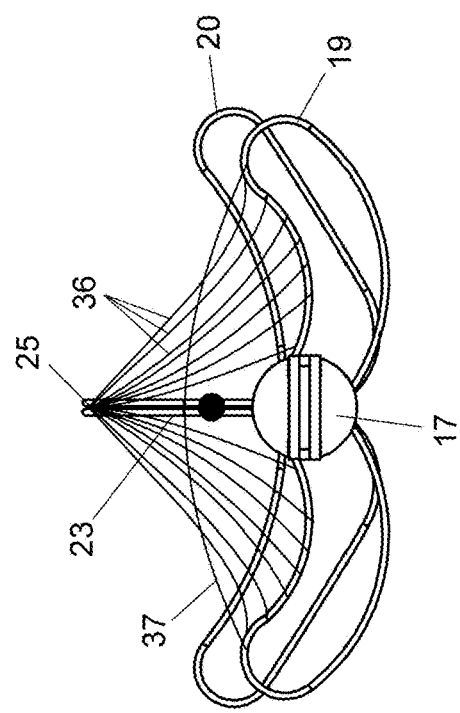
FIG. 2 is a top view of a mitral valve implant.

As shown in FIG. 2, FIG. 3 and FIG. 4 the implant comprises a support structure 16 configured to be arranged on and fixed to the annulus or to at least one of the first and second native first leaflets of the mitral valve. The support structure 16 comprises an upper support element 17 to be arranged on a superior surface of the annulus or of the at least one native leaflet and a lower support element 18 to be arranged on an inferior surface of the annulus or of the at least one native leaflet. The upper and the lower support elements 17 and 18 each comprises curved wires 19,20 made of a shape memory alloy, such as nitinol. Preferably, the curved wires are in the shape of at least two wings extending outwardly from a central support 21,22. The implant further comprising an arm 23 fixed to the lower support element 18 and having a bend 24 so that the free end of the arm faces away from the lower support element 18. The free end carries an eye 25 for holding one end of retention means, such as a net or flexible wires or yarn. In the exemplar embodiment shown in FIGS. 2, 3 and 4, the retentions means comprises a plurality of yarns 36, each extending from the wings 19 to the eye 25. The yarns 36 are fixed to the wings 19 in a manner evenly distributed along the length of the wings 19. Further, a yarn 37 is provided that extends in a direction crossing the yarns 36. The yarns 37 is connected to the yarns 36 at each crossing point, e.g. by gluing, bonding or welding, so as to maintain a net-like structure, wherein the yarns 36 are kept at a distance from each other. The function of the yarns 36 is to prevent prolapse of the at least one native leaflet.

In order to be able to fix the yarns 36 to the native leaflet a fixing element 39 is provided on a centrally located yarn 36 at the hinge point between the free valve surface and coaptation. In case of larger prolapses this mechanism of retention mechanisms can be doubled or multiplied.

Figure 5:
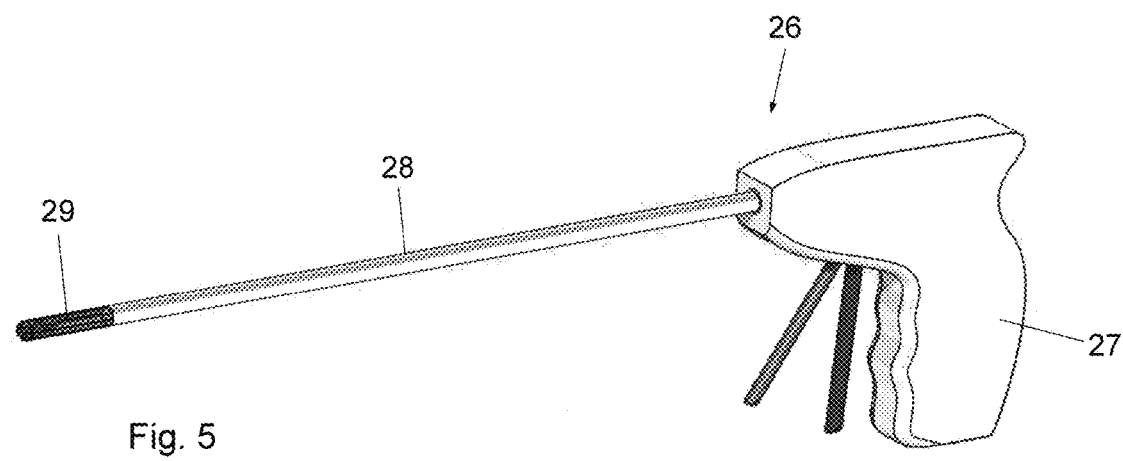
FIG. 5 is a perspective view of a deployment instrument for deploying the mitral valve implant into the human heart.

The deployment instrument for deploying the implant to the human heart is depicted in FIG. 5. The instrument 26 comprises a hand piece 27 and a flexible shaft 28, the distal free end of which is designed as a tubular housing 29 comprising two half-shells, a first half-shell 30 housing the upper support element 17 and a second half-shell 31 housing the lower support element 18. The wings 19 and 20 are arranged in a folded state so as to fit into the limited space provided inside the tubular housing 29.

Figure 6:
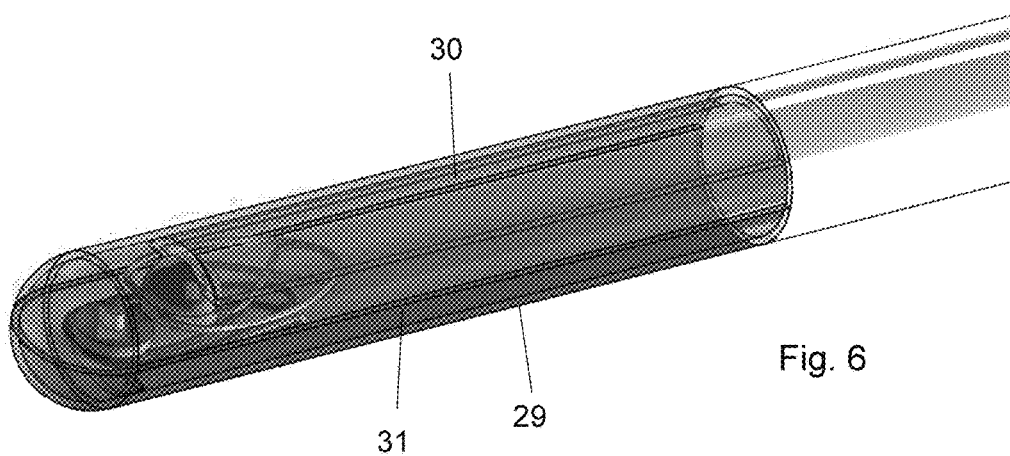
FIG. 6 is a perspective view of the folded mitral valve implant arranged in the deployment instrument.
Figure 7:
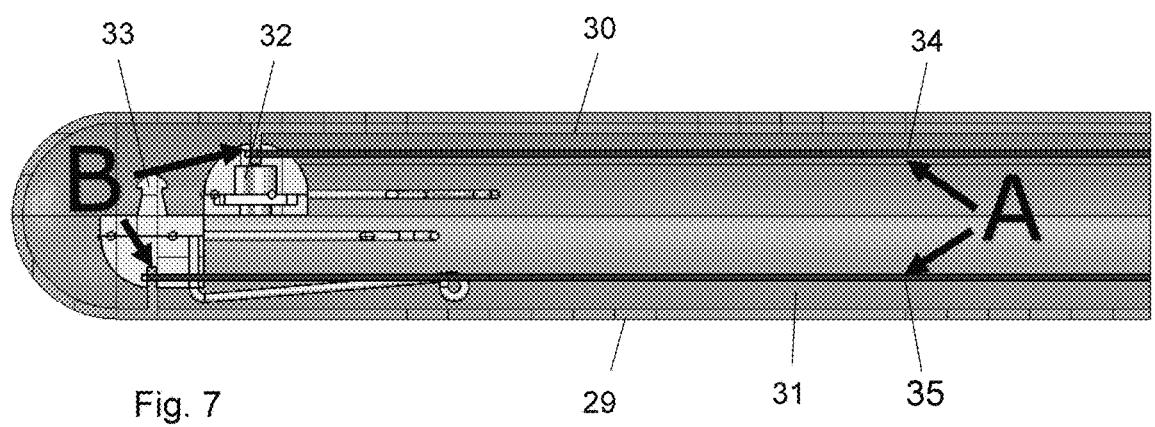
FIG. 7 shows a cross sectional view of FIG. 5, FIG. 8 to 13 are schematic illustrations of the consecutive steps of deploying and fixing a mitral valve implant in a human mitral valve.
Figure 8:
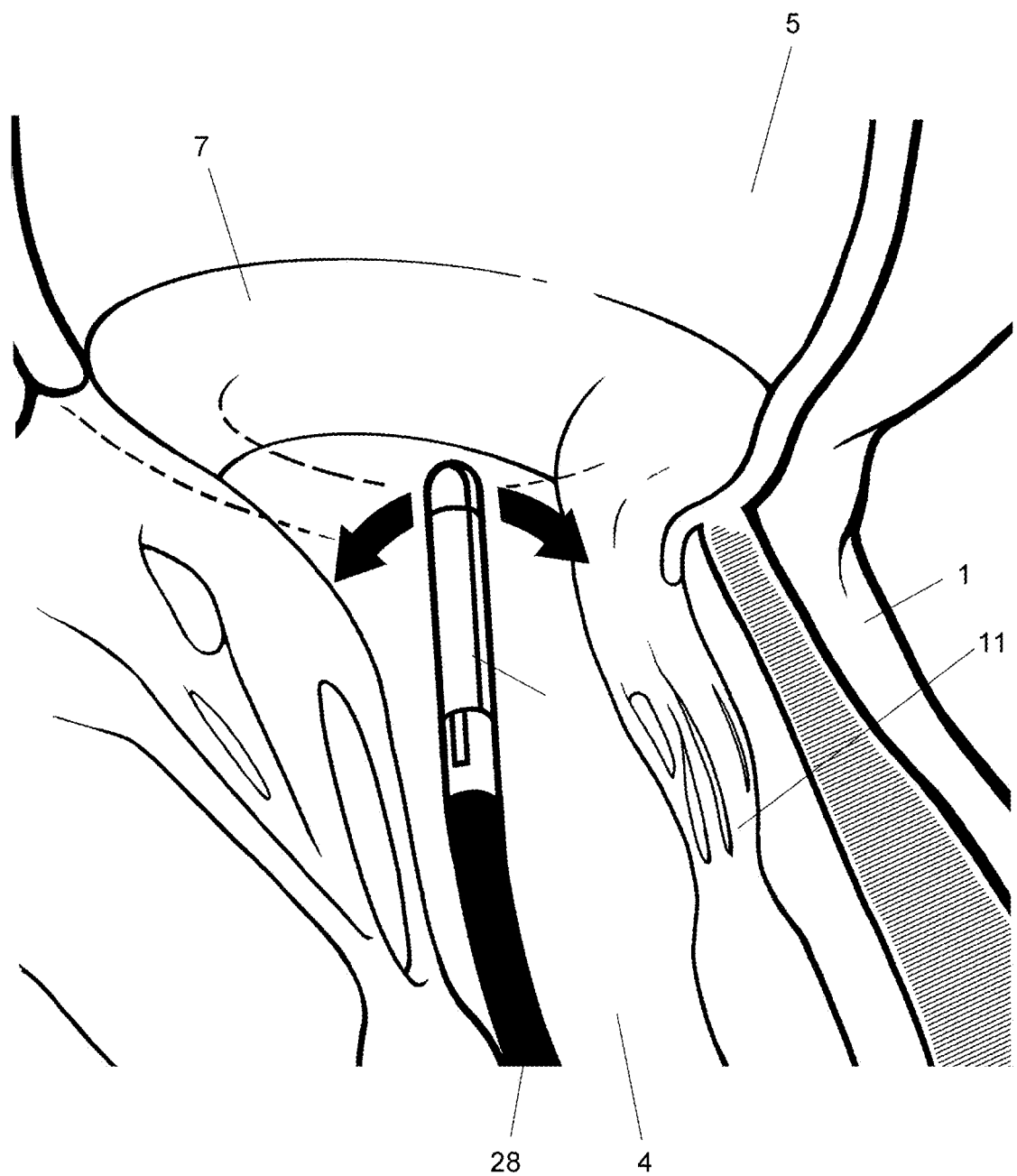

As can be seen in the illustration according to FIG. 6 and in the cross section according to FIG. 7 the upper support element 17 and the lower support element 18 are arranged in the tubular housing so as to be offset in the longitudinal direction and separated from each other. The upper and the lower support elements 17 and 18 each comprise connection means 32 and 33 cooperating which each other for interconnecting the upper and the lower support elements 17 and 18 while clamping a section of the annulus or of the at least one native leaflet between the upper support element 17 and the lower support element 18, wherein the connection means 33 of the lower support element 18 are configured as a penetrating section, in particular a recessed pin 33 configured to penetrate the annulus or the at least one native leaflet for being connected with the connection means 32 of the upper support element 17. The connection means 32 are configured as a bore, into which the pin 33 can immerse and fixed in the immersed position by means of a snap mechanism.

The first half-shell 30 and the second half-shell 31 are able to swing open by means of hinges 34 and 35 (FIG. 7).

FIG. 8 to 13 are schematic illustrations of the consecutive steps of deploying and fixing a mitral valve implant in a human mitral valve 7. In a first step, the flexible shaft 28 together with the tubular housing 29 is advanced into the left ventricle 4 of the human heart 1 transseptally, transapically or through the ascending aorta 9. Further, the tubular housing 29 is advanced from the left atrium 4 towards the mitral valve 7 in order to be placed in immediate vicinity of a leaflet of the mitral valve.

Figure 9:
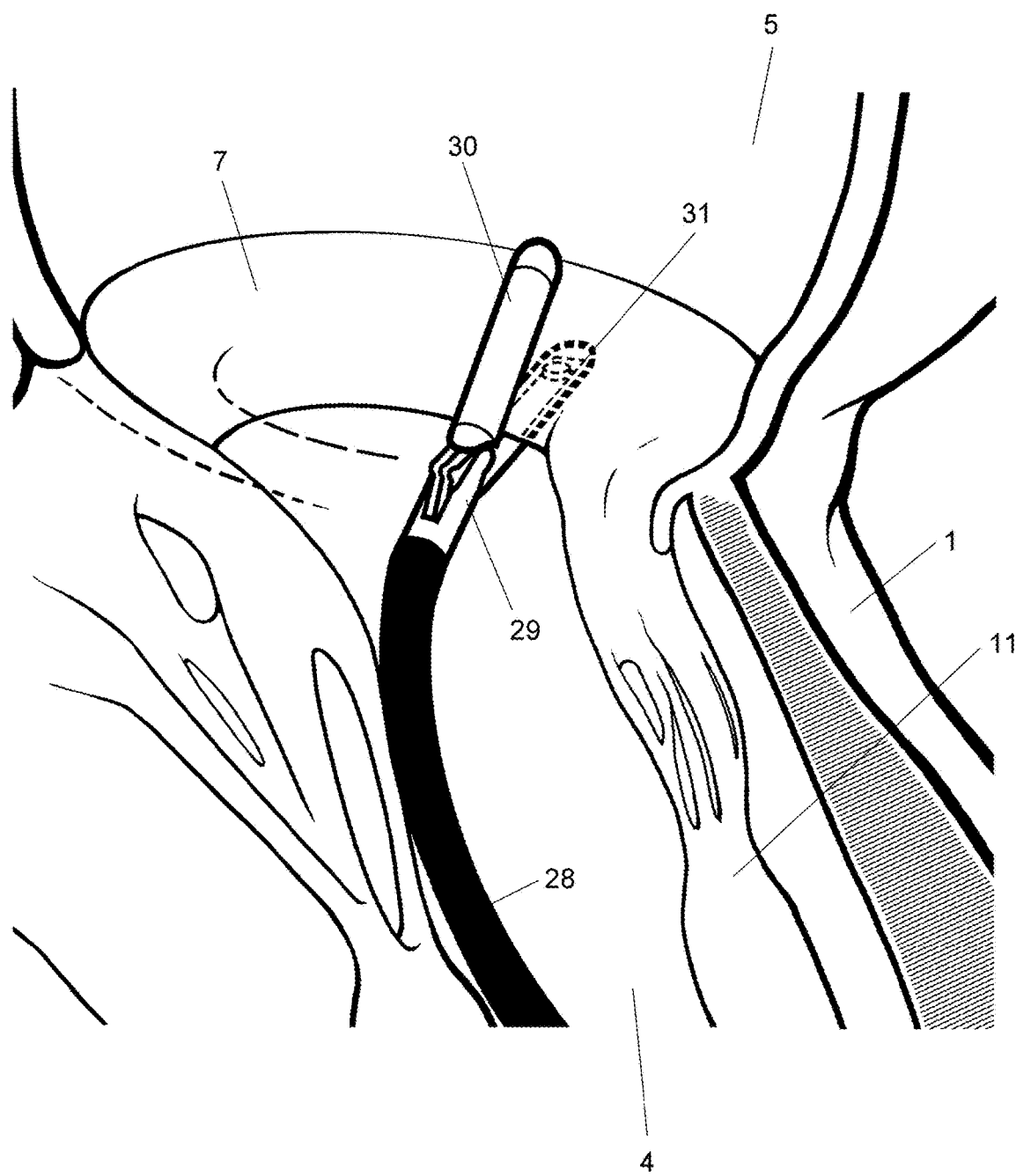

In this position, the half shells 30 and 31 of the tubular housing 29 are swung open, as can be seen in FIG. 9, and the tubular housing 29 is further advanced so that the leaflet of the mitral valve 7 is arranged between the upper shell 30 and the lower shell 31.

Figure 10:
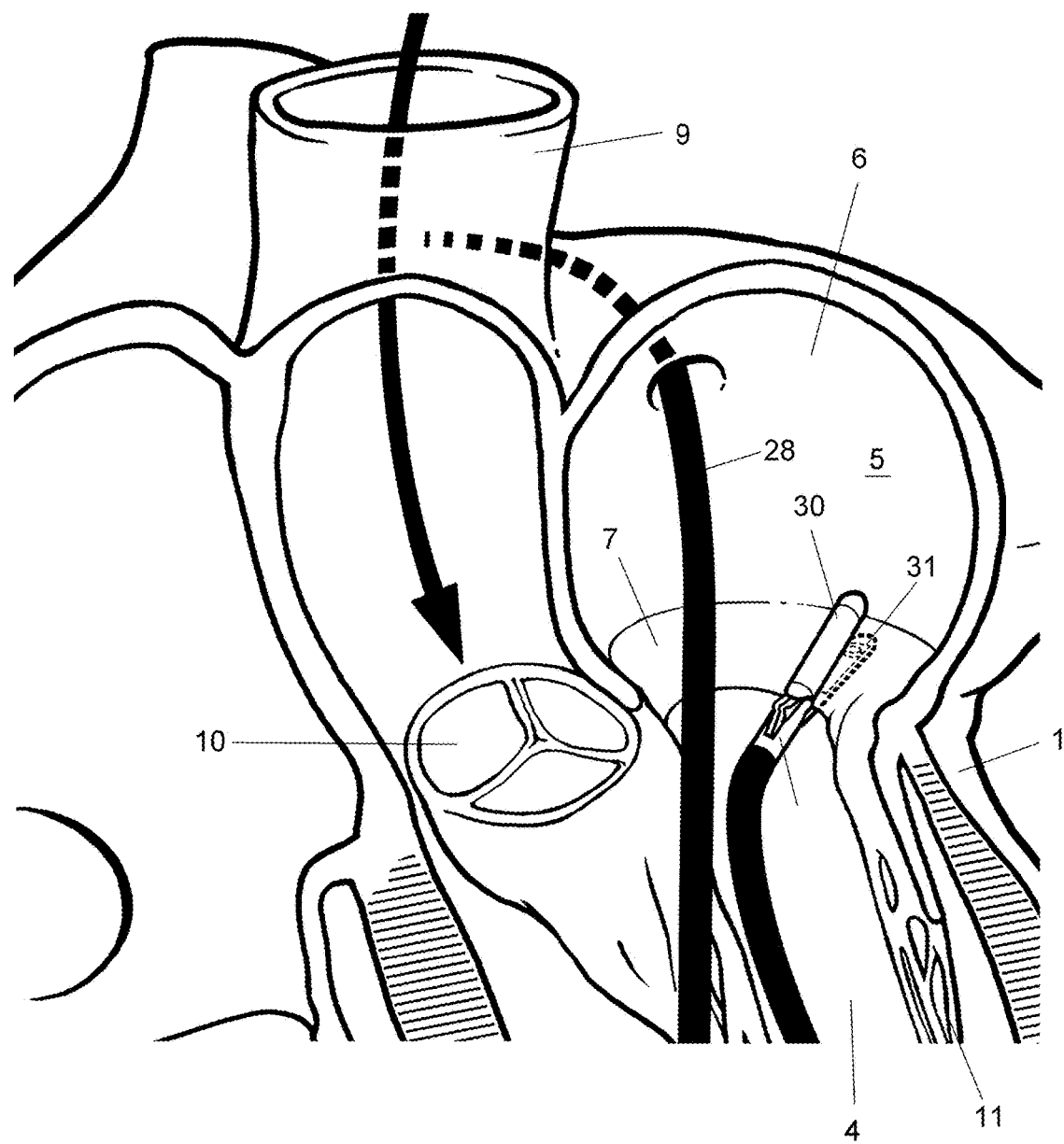
Figure 11:
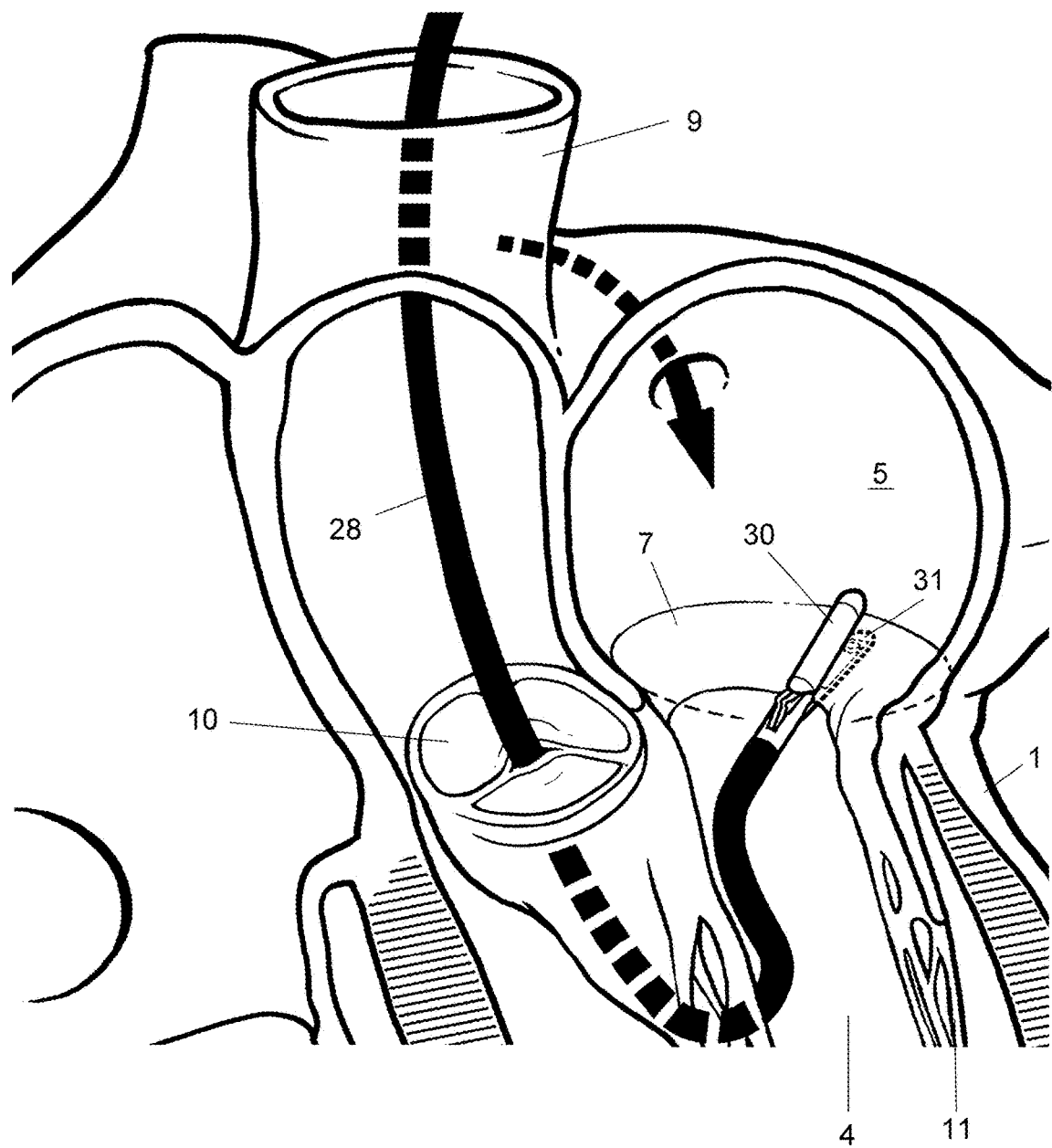

As illustrated in FIG. 10, the shaft 28 with the tubular housing 29 may be advanced into the left atrium 4 transseptally. Alternatively, as illustrated in FIG. 11, the shaft 28 with the tubular housing 29 may be advanced into the left atrium 4 through the ascending aorta 9 and the aortic valve 10.

Figure 12:
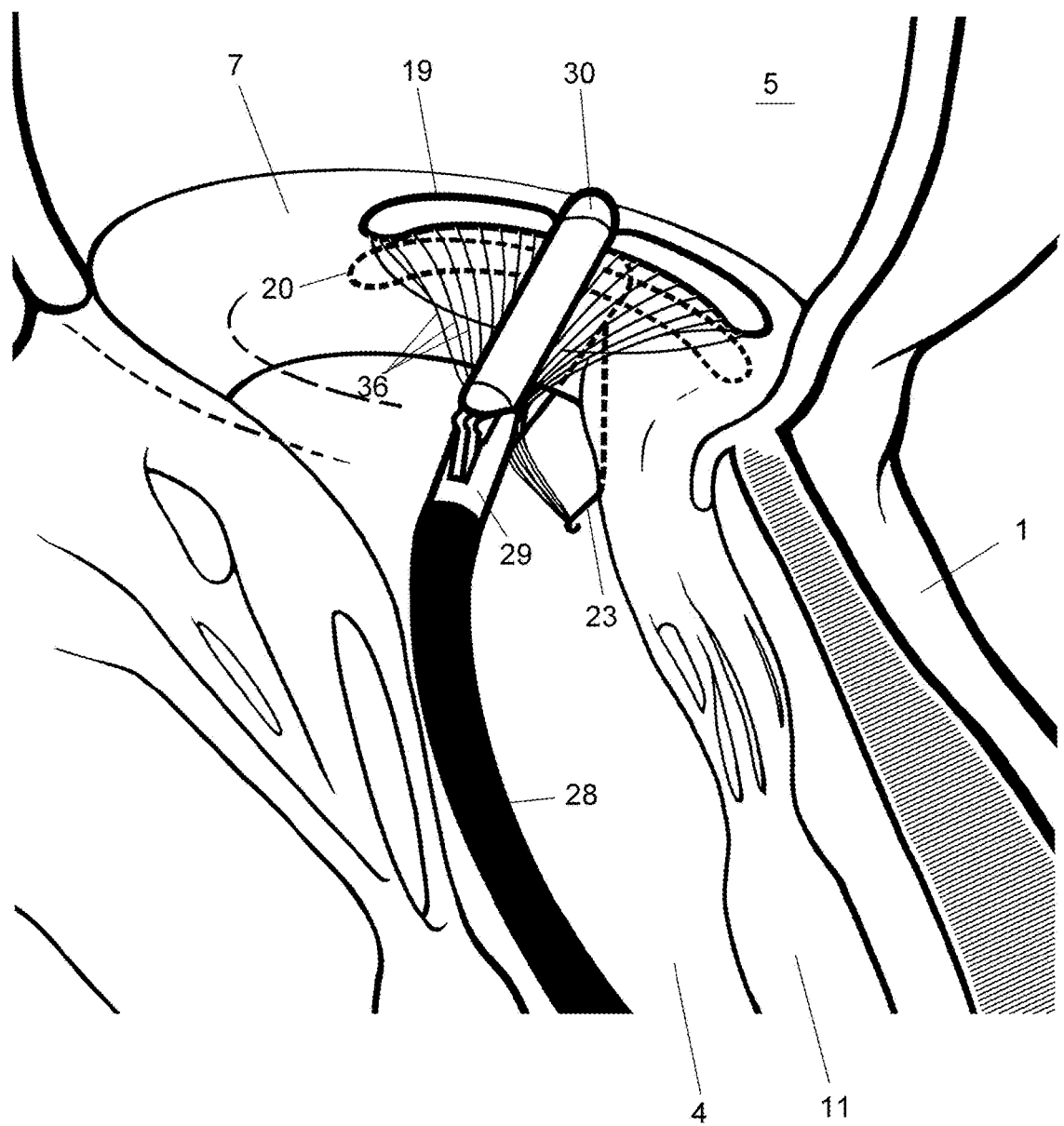

In a further step, illustrated in FIG. 12, the upper support element 17 including the wings 19 have been deployed form the upper half-shell 30 and the lower support element 18 including the wings 20 and the arm 23 have been deployed from the lower half-shell 31 of the tubular housing 29. The yarns 36 extend between the wings 19 and the arm 23. In particular, the yarns 36 extend from the wings 19 along the upper surface (the surface facing the left atrium 5) of the leaflet of the mitral valve 7, around the inner edge of the leaflet and down to the eye 25 arranged on the free end of the arm 23.

In a further step, the upper support element 17 and the lower support element 18 are fixed to the annulus or to the first or second native leaflet of the mitral valve 7. The fixing step comprises clamping a section of the annulus or of the first or second native leaflet if the mitral valve 7 between the upper support element 17 and the lower support element 18 by swinging the upper half-shell 30 and the lower half-shell 31 towards each other. During the clamping step connection means of the upper and the lower support elements 17,18 are connected with each other, wherein the pin 33 of the lower support element 18 penetrates the annulus or the first or second native leaflet of the mitral valve 7 and is introduced into the bore 32 of the upper support element 17, where it is fixed by a snapping action.

Figure 13:
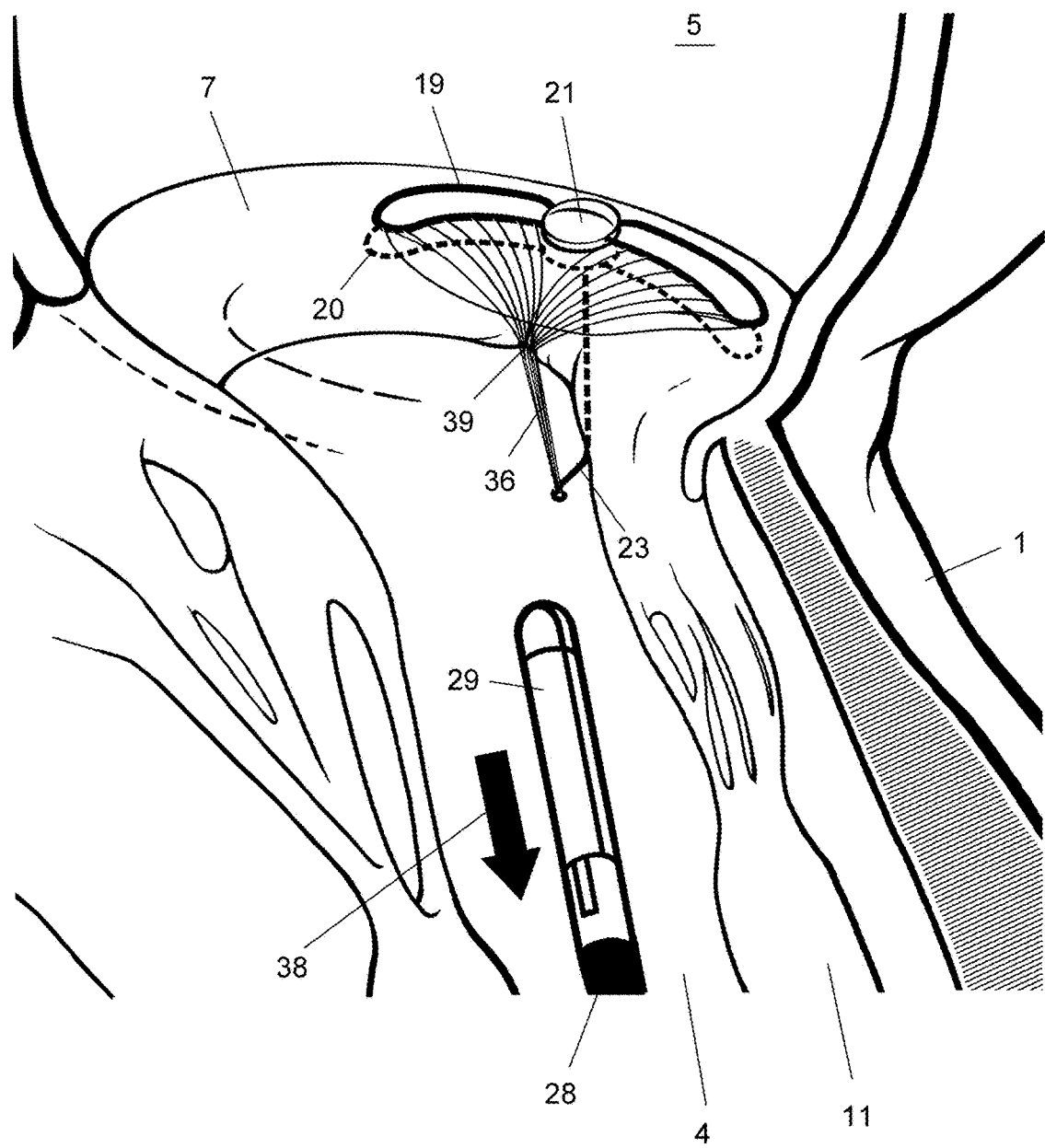

FIG. 13 illustrates the implant in its position fixed to the mitral valve 7. The yarns 36 of the implant prevent the leaflet of the mitral valve from prolapsing into the left atrium 5. After having fixed the implant to the mitral valve 7 and after having sixed the yarns 36 to the native leaflet in the region of its coaptation zone at 39, the shaft 28 together with the tubular housing 29 are retracted according arrow 38.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art. For instance a second penetration of the natural valve leaflet at the site of the coaptation (hinge point) for the artificial network or valve structure fixes the atrially facing leaflet structure and separating from the coaptation front. This secondary fixation point can be measured individually and may be construed for the personalized diseased valve.

Therefore, the above-described embodiments should be regarded as illustrative rather than restrictive. Accordingly, it should be appreciated that variations to those embodiments can be made by those skilled in the art without departing from the scope of the invention as defined by the following claims.

The invention claimed is:

1. An implant for improving coaptation of an atrioventricular valve, the atrioventricular valve having a native first leaflet, a native second leaflet and an annulus, the implant comprising a support structure configured to be arranged on and fixed to the annulus or to at least one of the first and second native first leaflets, retention means fixed to the support structure so as to prevent prolapse of the at least one native leaflet, wherein the support structure comprises an upper support element to be arranged on a superior surface of the annulus or of the at least one native leaflet and a lower support element to be arranged on an inferior surface of the annulus or of the at least one native leaflet, the upper and the lower support elements each comprising connection means cooperating which each other for interconnecting the upper and the lower support element while clamping a section of the annulus or of the at least one native leaflet between the upper support element and the lower support element, at least one connection means comprises a penetrating section configured to penetrate the annulus or the at least one native leaflet for being connected with the other connection means, a deployment instrument with a distal end, the deployment instrument comprising a tubular housing, wherein the support structure and the retention means are deployable from a first position in which the support structure and retention means are arranged within the tubular housing into a second position in which the support structure is deployed, wherein the tubular housing comprising two half-shells in which a first half shell housing the upper support element and a second half-shell housing the lower support element, with the first and second half-shells are arranged to swing open so as to deploy the implant, the lower support element carries at least one holding arm for holding the retention means, and the retention means, when arranged in the tubular housing, on one end thereof, are connected to the lower support element, and on the other end thereof are connected to the upper support element.

2. The implant of claim 1, wherein the upper and the lower support elements are housed in the tubular housing in a separate, not interconnected manner.

3. The implant of claim 1, wherein the first and second half-shells are arranged at the distal end of the deployment instrument.

4. The implant of claim 1, wherein the retention means comprise a flexible net or a plurality of flexible wires or yarns.

5. The implant of claim 1, wherein the retention means comprise an artificial leaflet arranged on the upper support element.

6. The implant of claim 5, wherein the implant further comprises a flexible net, wires or yarns embedded into or fixed to the artificial leaflet.

7. The implant of claim 1, wherein the atrioventricular valve is a mitral valve and the at least one native leaflet is a posterior leaflet of the mitral valve.

* * * * *